(12) United States Patent  
Wu et al.

(10) Patent No.: US 10,543,042 B2  
(45) Date of Patent: Jan. 28, 2020

(54) FIBER OPTIC LASER SURGICAL INSTRUMENT HAVING A RADIAL DISPERSION PATTERN

(71) Applicant: COVIDIEN LP, Mansfield, MA (US)

(72) Inventors: Xinmin Wu, Shanghai (CN); Zhongchi Luo, Shanghai (CN); Dang Xie, Shanghai (CN); Ruoxi Sun, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 387 days.

(21) Appl. No.: 15/313,575

(22) PCT Filed: May 23, 2014

(86) PCT No.: PCT/CN2014/078243  
§ 371 (c)(1),  
(2) Date: Nov. 23, 2016

(87) PCT Pub. No.: WO2015/176299  
PCT Pub. Date: Nov. 26, 2015

(65) Prior Publication Data  
US 2017/0189116 A1    Jul. 6, 2017

(51) Int. Cl.  
*A61B 18/18* (2006.01)  
*A61B 18/20* (2006.01)  
(Continued)

(52) U.S. Cl.  
CPC ............... *A61B 18/20* (2013.01); *A61N 5/06* (2013.01); *A61N 5/0601* (2013.01);  
(Continued)

(58) Field of Classification Search  
USPC .......................................................... 606/15  
See application file for complete search history.

(56) References Cited

U.S. PATENT DOCUMENTS 3,858,577 A    1/1975  Bass et al.  
4,871,233 A   10/1989  Sheiman  
(Continued)

FOREIGN PATENT DOCUMENTS

CN    200987836 Y   12/2007  
CN    201200612 Y    3/2009  
(Continued)

OTHER PUBLICATIONS

Notification of the First Office Action issued in corresponding Chinese Application No. 201480079159.5 dated Aug. 2, 2018, with English translation, 18 pages.  
(Continued)

*Primary Examiner* — Aaron F Roane  
(74) *Attorney, Agent, or Firm* — Carter, DeLuca & Farrell LLP

(57) ABSTRACT

A fiber optic probe that eliminates extreme tip temperatures by radiating laser energy in a radial, 360° pattern from the surface of an exposed fiber optic tip is disclosed. In an embodiment, a fiber optic core is configured to operatively engage with a source of laser energy at a proximal end of the fiber optic tip, and, at a distal end of the fiber optic tip, includes a plurality of refracting surfaces configured to disperse laser energy in a radial pattern. In one embodiment, the refracting surfaces may be arranged as a plurality of annular prisms defined around the fiber core. In another embodiment, the refracting surfaces may be arranged as a plurality of concave lenses defined in the fiber optic tip. The temperature distribution of the disclosed probes is controlled and uniform, and may be tailored to radiate laser energy in any desired pattern which may be suitable to achieve an intended objective.

19 Claims, 12 Drawing Sheets

(51) Int. Cl.
   *A61N 5/06* (2006.01)
   *A61B 18/22* (2006.01)
   *A61N 5/067* (2006.01)

(52) U.S. Cl.
   CPC ............ *A61B 2018/2222* (2013.01); *A61B 2018/2244* (2013.01); *A61B 2018/2272* (2013.01); *A61N 2005/067* (2013.01)

(56) References Cited

U.S. PATENT DOCUMENTS

| | | | |
|---|---|---|---|
| 5,078,711 A | | 1/1992 | Kakami et al. |
| 5,196,005 A | | 3/1993 | Doiron et al. |
| 5,280,788 A | | 1/1994 | Janes et al. |
| 5,330,465 A | | 7/1994 | Doiron et al. |
| 5,505,723 A | * | 4/1996 | Muller ............ A61F 9/008 606/10 |
| 5,772,657 A | | 6/1998 | Hmelar et al. |
| 5,953,477 A | | 9/1999 | Wach et al. |
| 6,144,791 A | | 11/2000 | Wach et al. |
| 6,347,178 B1 | | 2/2002 | Edwards et al. |
| 6,366,726 B1 | | 4/2002 | Wach et al. |
| 7,620,290 B2 | | 11/2009 | Rizoiu et al. |
| 2005/0137587 A1 | | 6/2005 | Nield et al. |
| 2005/0281530 A1 | | 12/2005 | Rizoiu et al. |
| 2007/0179488 A1 | * | 8/2007 | Trusty ............ A61B 18/22 606/16 |
| 2007/0263975 A1 | | 11/2007 | Boutoussov et al. |
| 2008/0317429 A1 | | 12/2008 | Boutoussov et al. |
| 2009/0240242 A1 | | 9/2009 | Neuberger |
| 2011/0098572 A1 | | 4/2011 | Chen et al. |
| 2013/0114927 A1 | | 5/2013 | Smith et al. |

FOREIGN PATENT DOCUMENTS

| | | |
|---|---|---|
| CN | 101970049 A | 2/2011 |
| CN | 102438539 A | 5/2012 |
| JP | S638239 A | 1/1988 |
| WO | 201116126 A1 | 2/2011 |

OTHER PUBLICATIONS

PCT International Search Report in corresponding Application No. PCT/CN2014/078243, 5 pages.

Supplementary European Search Report dated Jan. 11, 2018 in corresponding European Patent Application No. 14892557.

Chinese Office Action issued in corresponding Appl. No. CN 201480079159.5 dated Apr. 2, 2019, together with English language translation (18 pages).

* cited by examiner (Existing)

(Existing)

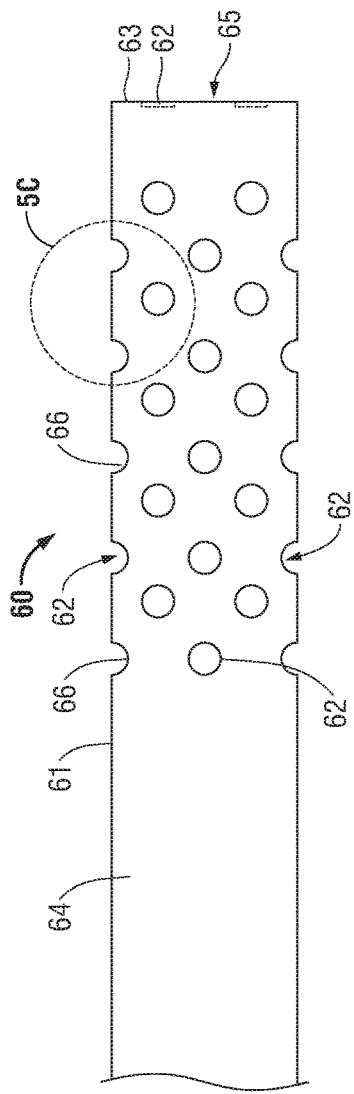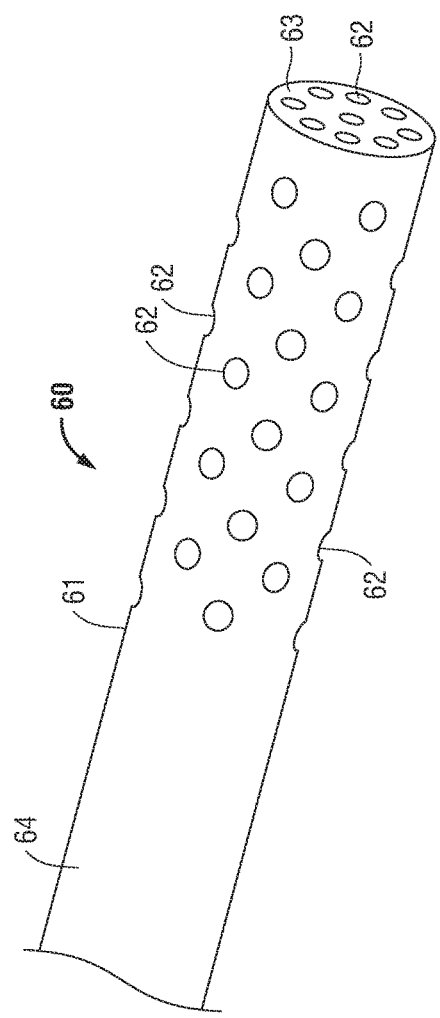
FIG. 5A
FIG. 5B

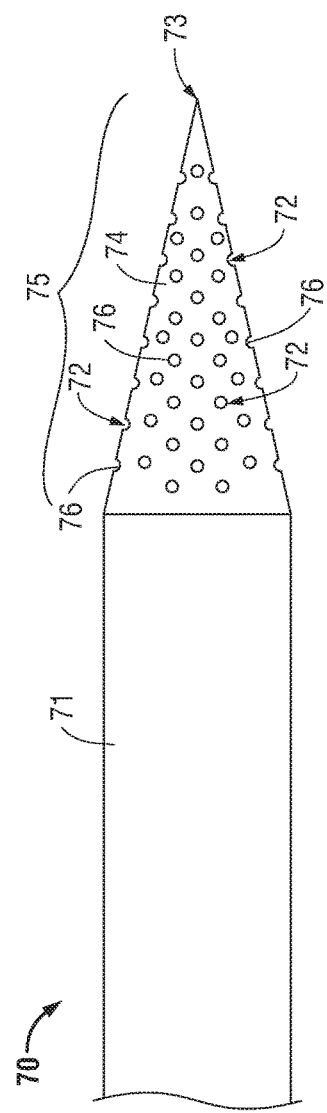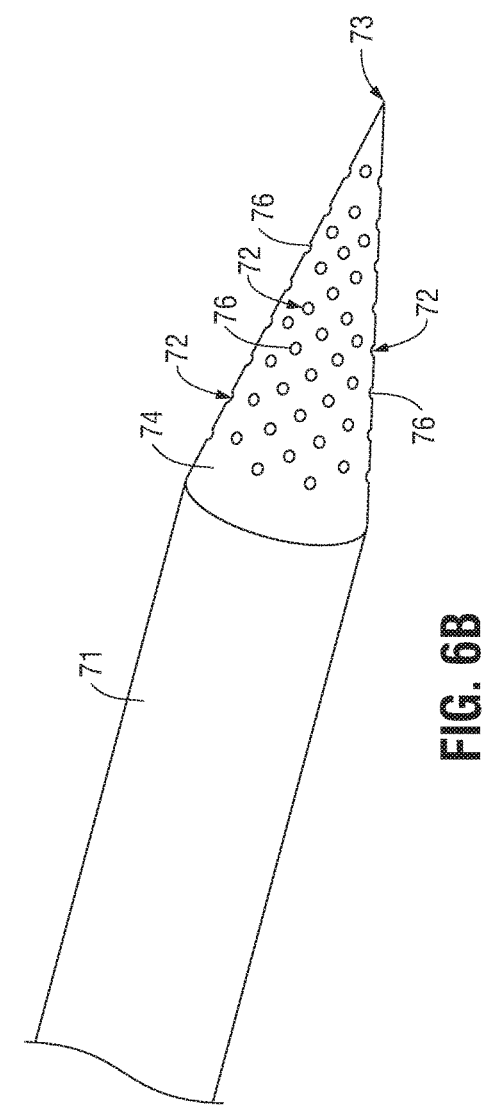
FIG. 6A
FIG. 6B

FIBER OPTIC LASER SURGICAL INSTRUMENT HAVING A RADIAL DISPERSION PATTERN

CROSS REFERENCE TO RELATED APPLICATION

The present application is a U.S. National Stage Application under 35 U.S.C. § 371(a) of PCT/CN2014/078243 filed May 23, 2014, the entire contents of which are incorporated by reference herein.

BACKGROUND

1. Technical Field

The present disclosure relates generally to surgical instruments and, more particularly, to a laser ablation instrument having a fiber optic output tip which utilizes a micro-prism structure to deliver a uniform radial distribution pattern.

2. Background of Related Art

Laser-based instruments are becoming increasingly accepted in the medical field for use in minimally invasive procedures such as laser laparoscopy. For example, laser therapy is a widely accepted modality for tissue ablation procedures. Laser-based instruments are known to utilize fiber optic cables to deliver laser energy from the laser light source to targeted tissue.

Fiber optic cables are composed of one or more transparent glass or plastic fibers through which light is efficiently conducted with minimal loss. The light-conducting fibers, called the core, are encased in a second medium, called the cladding layer, which has an index of refraction lower than that of the core to provide total internal reflection of the rays propagating though the core. That is, light traveling through the fiber bounces at shallow angles and stays completely within the fiber because light hits the interface between the core and cladding at an angle less than the critical angle. At these angles, light does not pass through to the second medium, but rather, continues reflecting within the core until it reaches the terminus, or end of the fiber.

A surgeon who performs procedures using existing laser-based instruments is often challenged with non-uniform temperature distribution, because laser dispersion through the fiber terminus radiates from a point source at the instrument tip in a generally conical pattern, causing the temperature at the tip to increase rapidly to 800° C.-1,300° C. while rapidly decreasing with distance from the tip. Such wide temperature variations may have drawbacks. For example, the tendency for the temperature to decrease with distance from the fiber tip may unnecessarily complicate vascular ablation procedures.

SUMMARY

In one aspect, the present disclosure is directed to an instrument for laser surgery. In an embodiment, the disclosed instrument includes a cladding having a first refractive index and a fiber optic core coaxially disposed within the cladding and having a second refractive index that is higher than the first refractive index. The fiber optic core is configured to operatively engage with a source of laser energy at a proximal end of the fiber optic core. The instrument includes a fiber optic tip formed on a distal end of the fiber optic core and configured to extend outwardly from the cladding. The instrument further includes a plurality of refracting surfaces formed around the fiber optic tip. Each refracting surface is formed at least at one angle to a longitudinal axis of the fiber optic tip and configured to disperse the laser energy in a radial pattern.

In some embodiments, the instrument further includes a plurality of annular prisms defined around the fiber optic tip. In some embodiments, each one of the plurality of refracting surfaces is disposed on a corresponding one of the plurality of annular prisms. In some embodiments, a diameter of each one of the plurality of annular prisms decreases as the distance of each one of the annular prisms from a distal end of the fiber optic tip decreases.

In some embodiments, the angle between each refracting surface and a longitudinal axis of the fiber optic core varies as a function of distance between each refracting surface and a distal end of the fiber optic tip. In some embodiments, the angle of a first refracting surface is greater than the angle of a second refracting surface that is farther than the first refracting surface from the distal end of the fiber optic tip. In some embodiments, the angle of each refracting surface decreases as the distance of each refracting surface from the distal end of the fiber optic tip decreases.

In some embodiments, each one of the plurality of refracting surfaces includes a concave lens defined in the fiber optic tip. In some embodiments, a distal portion of the fiber optic tip on which the concave lenses are defined is tapered.

In another aspect, the present disclosure is directed to a laser surgery system. The laser surgery system includes a source of laser energy, a controller operatively coupled to the source of laser energy, and a laser surgical instrument. The laser surgical instrument of the laser surgery system includes a cladding having a first refractive index and a fiber optic core surrounded by the cladding and having a second refractive index that is higher than the first refractive index. The fiber optic core is configured to operatively engage with the source of laser energy at a proximal end of the fiber optic core. The instrument includes a fiber optic tip formed on a distal end of the fiber optic core and a plurality of refracting surfaces formed around the fiber optic tip. Each refracting surface is formed at least at one angle to a longitudinal axis of the fiber optic tip and configured to disperse the laser energy in a radial pattern.

In some embodiments, the instrument includes a plurality of annular prisms defined around the fiber optic tip. In some embodiments, each one of the plurality of refracting surfaces is disposed on a corresponding one of the plurality of annular prisms. In some embodiments, a diameter of each one of the plurality of annular prisms decreases as the distance of each one of the annular prisms from a distal end of the fiber optic tip decreases.

In some embodiments, the angle between the refracting surface and a longitudinal axis of the fiber optic core varies as a function of distance between each refracting surface and a distal end of the fiber optic tip. In some embodiments, the angle of a first refracting surface is greater than the angle of a second refracting surface that is farther than the first refracting surface from the distal end of the fiber optic tip. In some embodiments, the angle of each refracting surface decreases as the distance of each refracting surface from the distal end of the fiber optic tip decreases.

In some embodiments, each one of the plurality of refracting surfaces includes a concave lens defined in the fiber optic tip. In some embodiments, a distal portion of the fiber optic tip on which the concave lenses are defined is tapered.

In some embodiments, the laser surgery system includes a power supply operatively coupled to the controller and/or the source of laser energy.

In yet another aspect, the present disclosure is directed to a method of treating tissue using a laser. In an embodiment, the method includes providing an instrument having a fiber optic core having, at a distal end of the fiber optic core, a plurality of refracting surfaces configured to disperse laser energy in a radial pattern. The method includes placing the distal end of the fiber optic core in proximity to targeted tissue, transmitting laser energy through the fiber optic core, and delivering the laser energy to the tissue in the radial pattern via the plurality of refracting surfaces.

BRIEF DESCRIPTION OF THE DRAWINGS

The above and other aspects, features, and advantages of the present disclosure will become more apparent in light of the following detailed description when taken in conjunction with the accompanying drawings in which:

FIG. 5A is a cross-sectional view of a fiber optic radial tip in accordance with another embodiment of the present disclosure;

FIG. 5B is a perspective schematic view of the fiber optic radial tip of FIG. 5A;

FIG. 6A is a cross-sectional view of a tapered fiber optic tip in accordance with yet another embodiment the present disclosure; and FIG. 6B is a perspective schematic view of the tapered fiber optic terminus of FIG. 6A.

DETAILED DESCRIPTION

Figure 1:
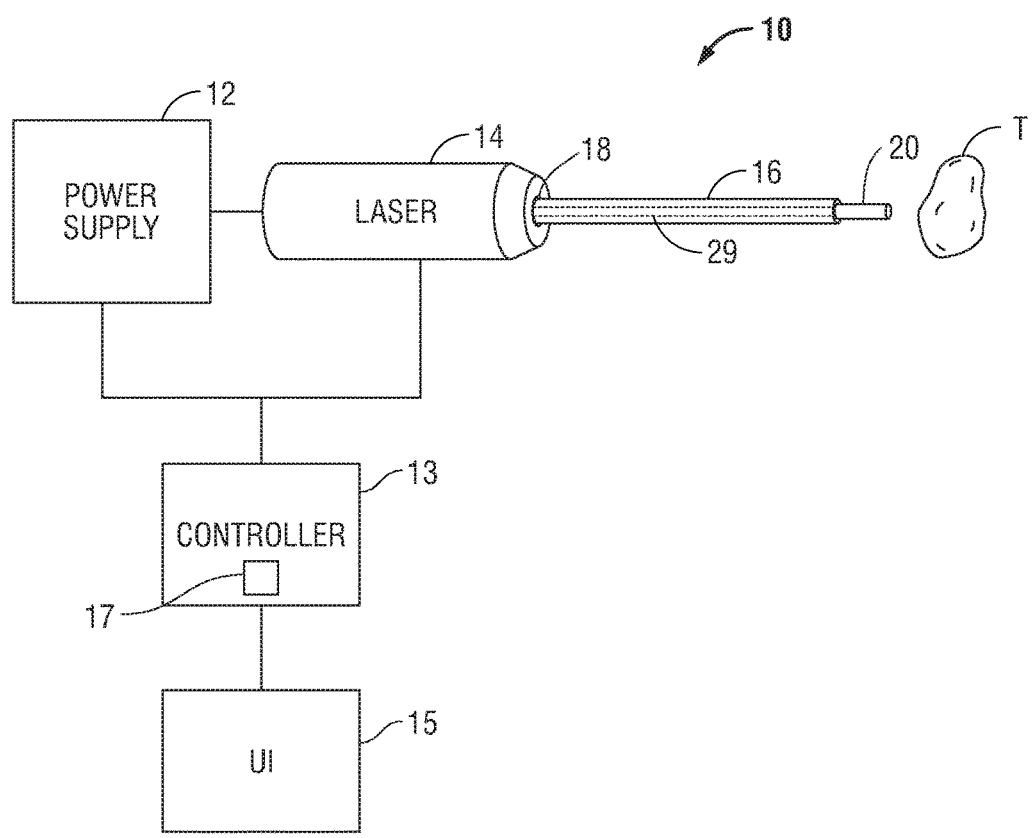
FIG. 1 is a schematic diagram of a laser surgery system in accordance with an embodiment of the present disclosure.

The present disclosure is directed to fiber optic probes that eliminate extreme tip temperatures by radiating laser energy in a radial, 360° pattern from the surface of an exposed fiber optic tip. In accordance with the present disclosure, the temperature distribution of the disclosed probes is controlled, uniform, and may be tailored to radiate laser energy in any desired pattern which may be suitable to achieve an intended objective. In one aspect, embodiments of the present disclosure enable a surgeon to treat, for example, vascular structures using a "segment-by-segment" approach, rather than the "point-by-point" approach necessitated by prior-art devices. In this manner, operative times may be decreased, which subsequently may improve patient outcomes and reduce recovery times. In addition, use of embodiments in accordance with the present disclosure may enable a surgeon to avoid complications arising from the extreme temperatures and sudden temperature gradients that are characteristic of prior-art devices. In another aspect, the described probe may be manufactured in various lengths and/or radiation patterns to suit particular interventional scenarios. For example, an elongate cylindrical profile may be provided for vascular procedures, while a longer, tapered profile may be provided for tumor ablation procedures.

Particular illustrative embodiments of the present disclosure are described hereinbelow with reference to the accompanying drawings; however, the disclosed embodiments are merely examples, which may be embodied in various forms. Well-known functions or constructions and repetitive matter are not described in detail to avoid obscuring the present disclosure in unnecessary or redundant detail. Therefore, specific structural and functional details described in this disclosure are not to be interpreted as limiting, but merely as a basis for the claims and as a representative basis for teaching one skilled in the art to variously employ the present disclosure in virtually any appropriately detailed structure.

As shown in the drawings and as described throughout the following description, and as is traditional when referring to relative positioning on an object, the term "proximal" refers to the end of the apparatus that is closer to the user and the term "distal" refers to the end of the apparatus that is farther from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

With reference to FIG. 1, a laser surgery system 10 in accordance with the present disclosure includes a power supply 12 that is configured to deliver activation energy to laser 14. Laser 14 may include any suitable structure capable of providing laser energy for surgical use, including without limitation, a $CO_2$ laser, an excimer laser, a semiconductor laser (e.g., a laser diode), or a fiber laser. Power supply 12 is configured to convert line voltage into a form suitable for operation of laser 14 and may include a linear power supply circuit and/or switched-mode voltage converter circuit. Laser surgery system 10 includes controller 13 which communicates with user interface 15 and which conveys one or more control signals to power supply 12 and/or laser 14 to facilitate operation of laser surgery system 10. For example, laser power level, pulse rate, pulse width, duty cycle, modulation, wavelength, operating voltage, etc. may be established either directly or indirectly via user interface 15 and communicated to power supply 12 and/or laser 14.

Controller 13 includes a storage unit 17 (e.g., non-volatile memory) that is configured to store calibration data, user preference data, treatment parameters, and the like. In embodiments, controller 13 may be configured to perform diagnostic functions, built in test (BIT) functions, and power-up self tests (POST), to identify any need to perform service and maintenance, to replace consumables, and so forth, in order to ensure proper functioning of the laser surgery system 10. A shaft 16 having a radial terminus 20 disposed at a distal end of the shaft 16 includes a fiber optic assembly 29 in operable communication with an output 18 of the laser 14 and configured to deliver laser energy to tissue T.

Figure 2A:
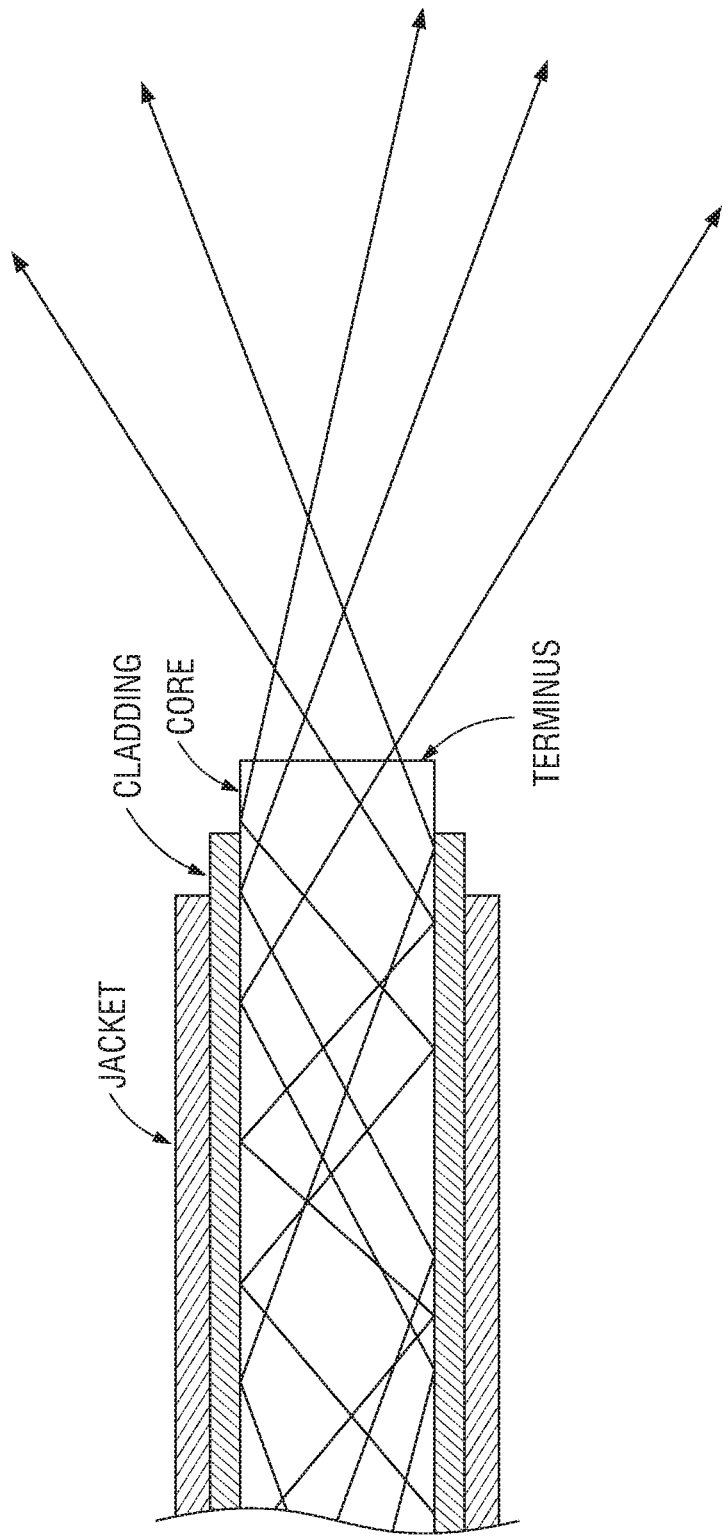
FIG. 2A is a cross-sectional view of an existing fiber optic terminus of an existing laser surgery instrument.
Figure 2B:
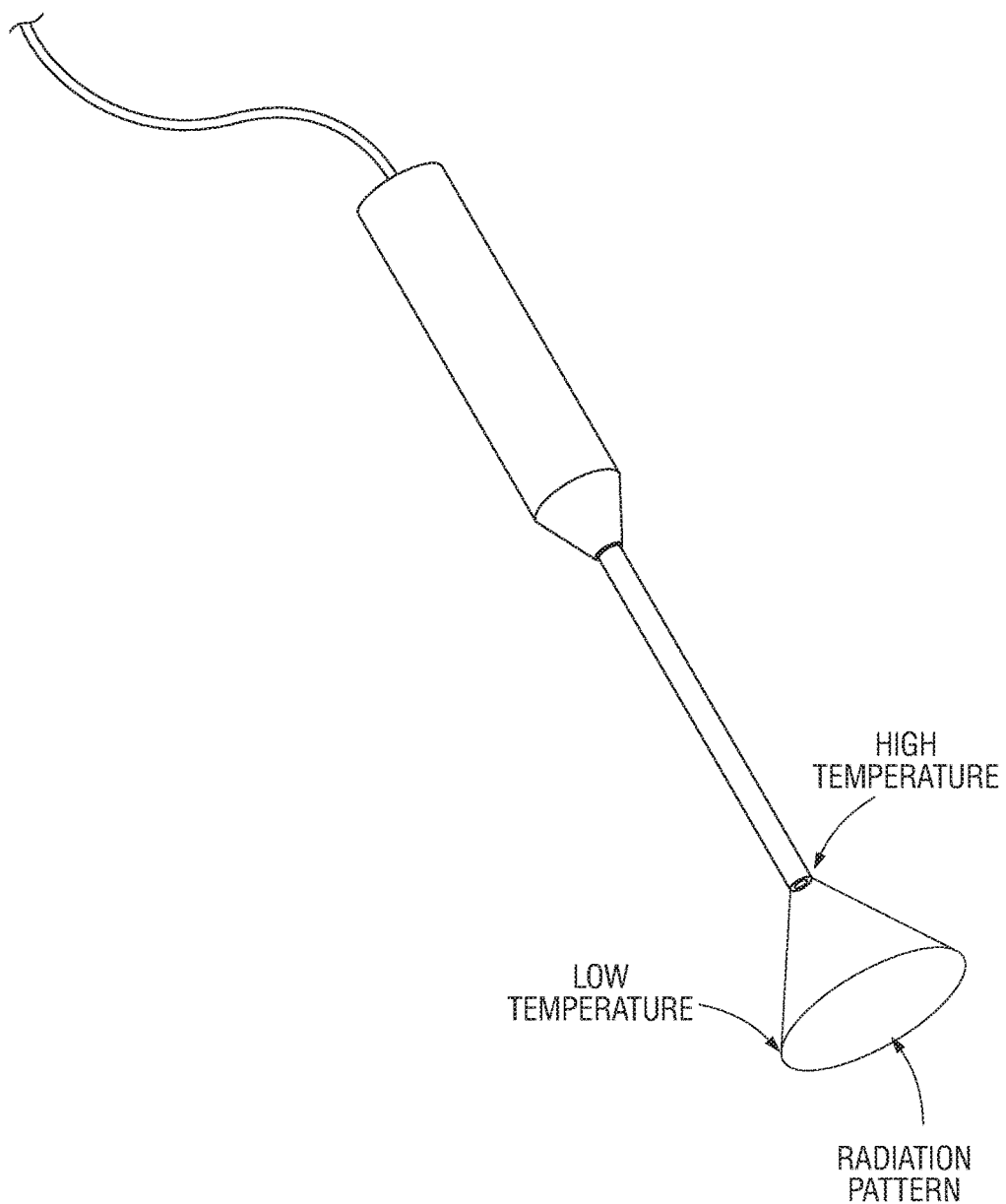
FIG. 2B is a perspective schematic view of a radiation pattern of an existing laser surgery instrument.

A fiber optic cable and terminus of an existing laser-based instrument is shown in FIGS. 2A and 2B. The core is the innermost portion of the fiber, which is surrounded by cladding, which, in turn, is encased in a protective jacket. The core transmits the light and has a higher refractive index than that of the cladding, which surrounds the core. By this arrangement, the light in the core intersects the boundary between the core and the cladding at an angle shallower than the critical angle based on the refractive indices of the core and the cladding, and therefore is reflected back into the core by total internal reflection. This repeats along the length of the fiber until the terminus is reached. At this point, because the light in the core intersects at an angle greater than the critical angle based on the refractive indices of the core and the air, the light is transmitted though the boundary of the terminus and the environment, and exits the fiber core. As illustrated in FIG. 2B, when the laser light exits at the terminus, the temperature radiation pattern is characterized by a generally conical shape having an apex at the terminus and widening distally from the terminus. Since the laser light is concentrated at the terminus, e.g., at the apex of the radiating pattern, the temperature at the terminus increases rapidly to 800° C.-1,300° C., which may be undesirable.

Figure 3A:
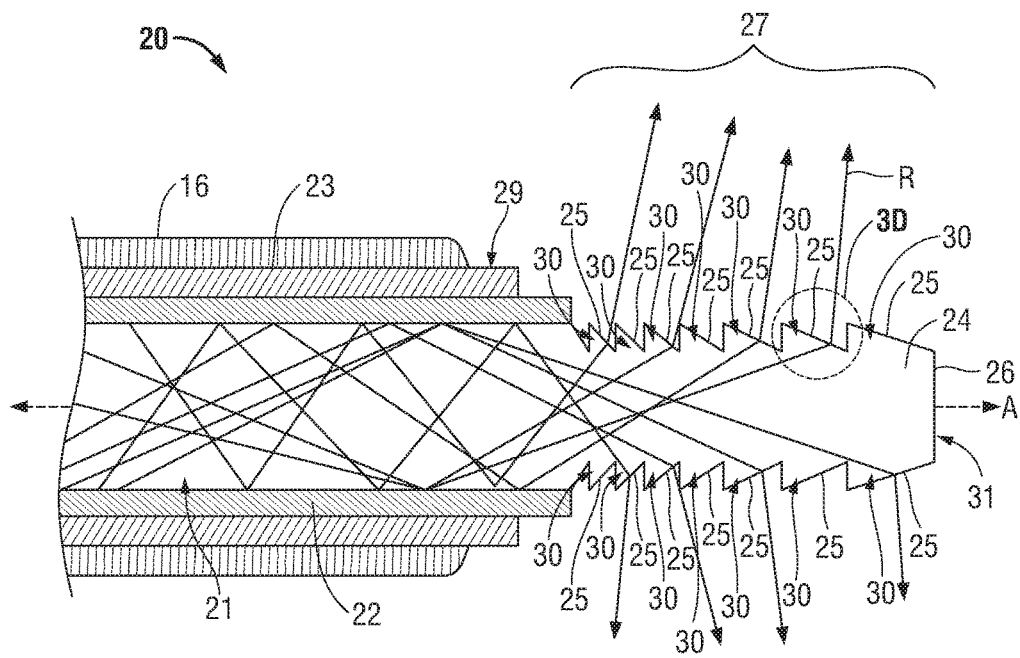
FIG. 3A is a cross-sectional view of a fiber optic radial terminus of a laser surgery instrument having a radial radiation pattern in accordance with an embodiment the present disclosure.
Figure 3D:
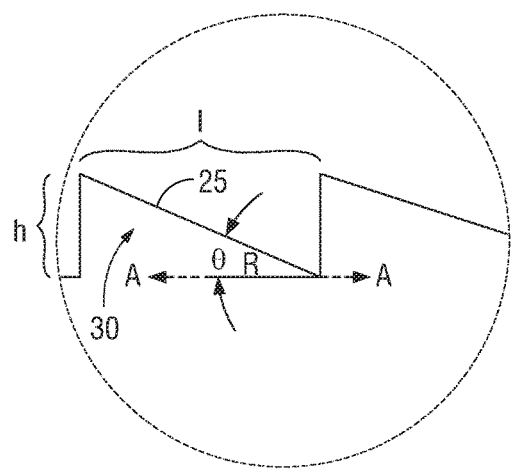
FIG. 3D is an enlarged, cross-sectional view of a portion of the fiber optic radial terminus of FIG. 3A.
Figure 3B:
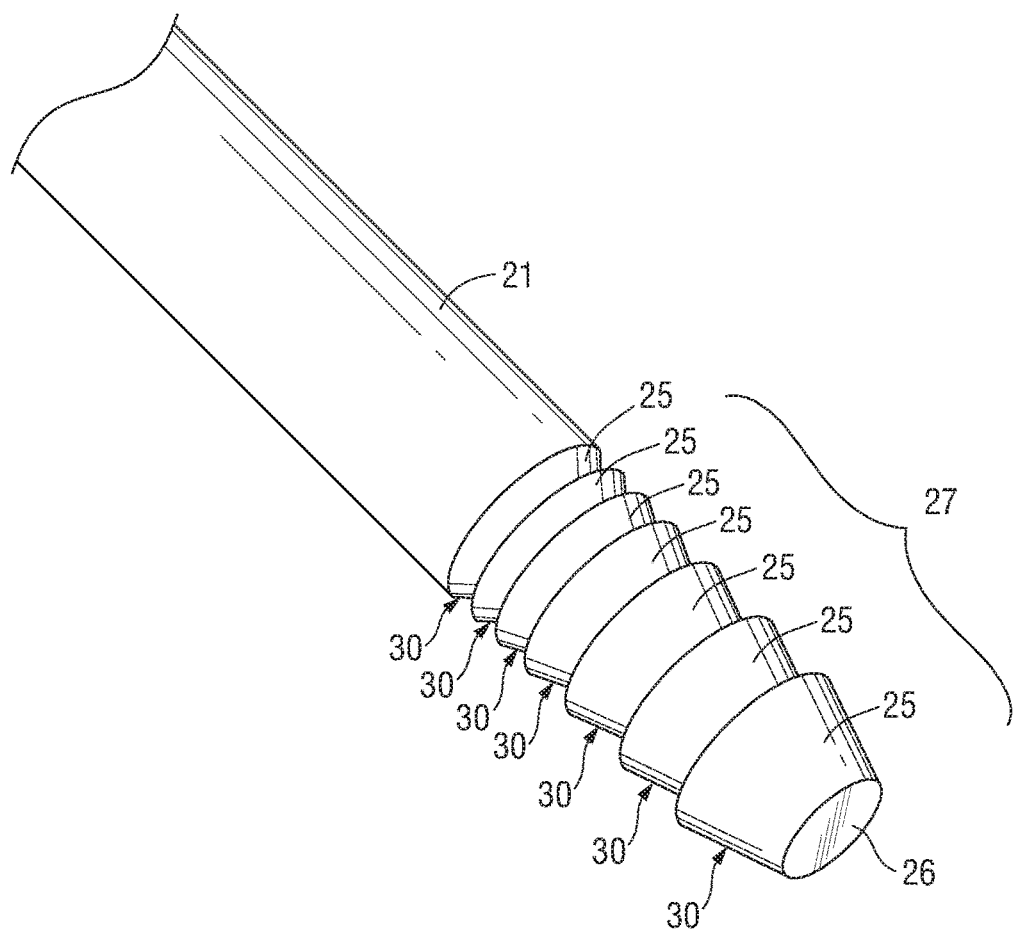
FIG. 3B is a perspective view of the fiber optic radial terminus of the laser surgery instrument of FIG. 3A in accordance with the present disclosure.
Figure 3C:
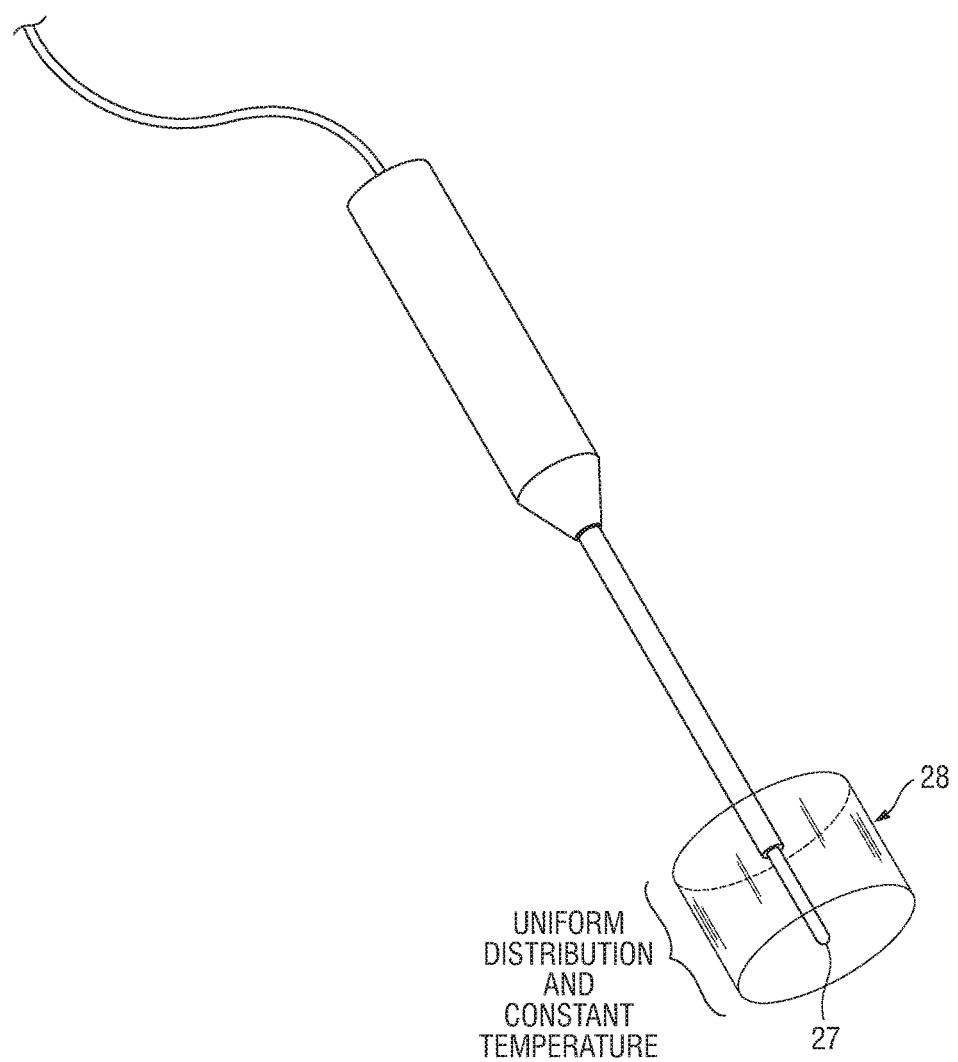
FIG. 3C is a perspective schematic view of a radial pattern of thermal radiation of the laser surgery instrument of FIG. 3A.

Turning now to FIGS. 3A, 3B, and 3C, a radial terminus 20 is disposed at a distal end of fiber optic assembly 29. Fiber optic assembly 29 includes a fiber core 21 which is transparent and has an index of refraction. The fiber core 21 has an elongate cylindrical shape and may be formed from glass (including, without limitation, silica, fluorozirconate, fluoroaluminate, chalcogenide, and sapphire glasses) or may be formed from transparent polymeric material, such as, without limitation, polymethyl methacrylate (a.k.a. acrylic polymer). The fiber core 21 is encased in cladding 22 which is formed from material having an index of refraction that is less than the index of refraction of the fiber core 21. The cladding 22, in turn, is encased in a jacket 23 that is configured to provide mechanical protection and support to the cladding 22 and the fiber core 21. The jacket 23 may be formed from any suitable material, such as, without limitation, polyvinyl chloride (PVC), polytetrafluoroethylene (PTFE), and so forth. Generally, the jacket 23 is formed from material that is optically opaque to reduce interference with and/or leakage of light transmitted through the fiber core 21. The fiber optic assembly 20 may include additional layers (not explicitly shown) which provide additional protection and/or modify a performance characteristic (e.g., optical property) of the fiber optic assembly 20.

A portion of the fiber core 21 extends distally beyond a distal end of the cladding 22, the jacket 22, and the shaft 16 to form a radial tip 27. The radial tip 27 includes a series of annular prisms 30 defined around the radial tip 27, with each prism 30 having a refracting surface 25. The refracting surface 25 is disposed at a prism angle $\theta_R$ relative to a longitudinal axis A corresponding to the centerline of the fiber core 21. This embodiment is best illustrated in FIGS. 3A, 3B, and 3D. The prism angle $\theta_R$ of each refracting surface 25 is related to the distance of the associated prism 30 from the distal end 26 of the radial tip 27. As seen in FIG. 3A, the prism angle $\theta_R$ of each successively distal prism 30 is less than that of the prior (immediately proximal) prism 30. By this arrangement, during use, the rays R of laser energy propagate distally through the fiber core 21, and eventually intersect one of the refracting surfaces 25 at an angle greater than the critical angle (thereby not meeting the conditions for total internal reflection) and thus exit the fiber core 21 in a radial pattern 28 (FIG. 3C). An opaque or semitransparent coating 31 may be disposed on a distal end 26 to reduce or eliminate laser emissions from distal end 26.

The prism angle $\theta_R$, prism height h, and prism length l may be arranged in accordance with the nature of the laser source and the numerical aperture of the fiber core 21. Thus, by tailoring the angle and the dimensions of the prisms 30, the distribution of rays exiting from the fiber core 21 can be tailored as required. In embodiments where the laser source intensity distribution and the numerical aperture are fixed, the prisms 30 are designed to obtain the uniform distributed radially emitted laser profile as shown in FIG. 3C, which, in turn, provides a constant temperature along the length of the radial tip 27.

Dimensions of the prism (i.e., the angle $\theta_R$, height h, and length l) may be dependent upon the wave length of the laser but are not dependent upon a type of the laser. That is, the lengthier the wave length of the laser is, the bigger the dimensions of the prism become and vice versa. In embodiments, the prism angle $\theta_R$ may range from 0 degree to 90 degree, and the prism height and length may range from 0.1 mm to 1.0 mm. The numeral aperture may range from 0.1 to 0.5.

Figure 4A:
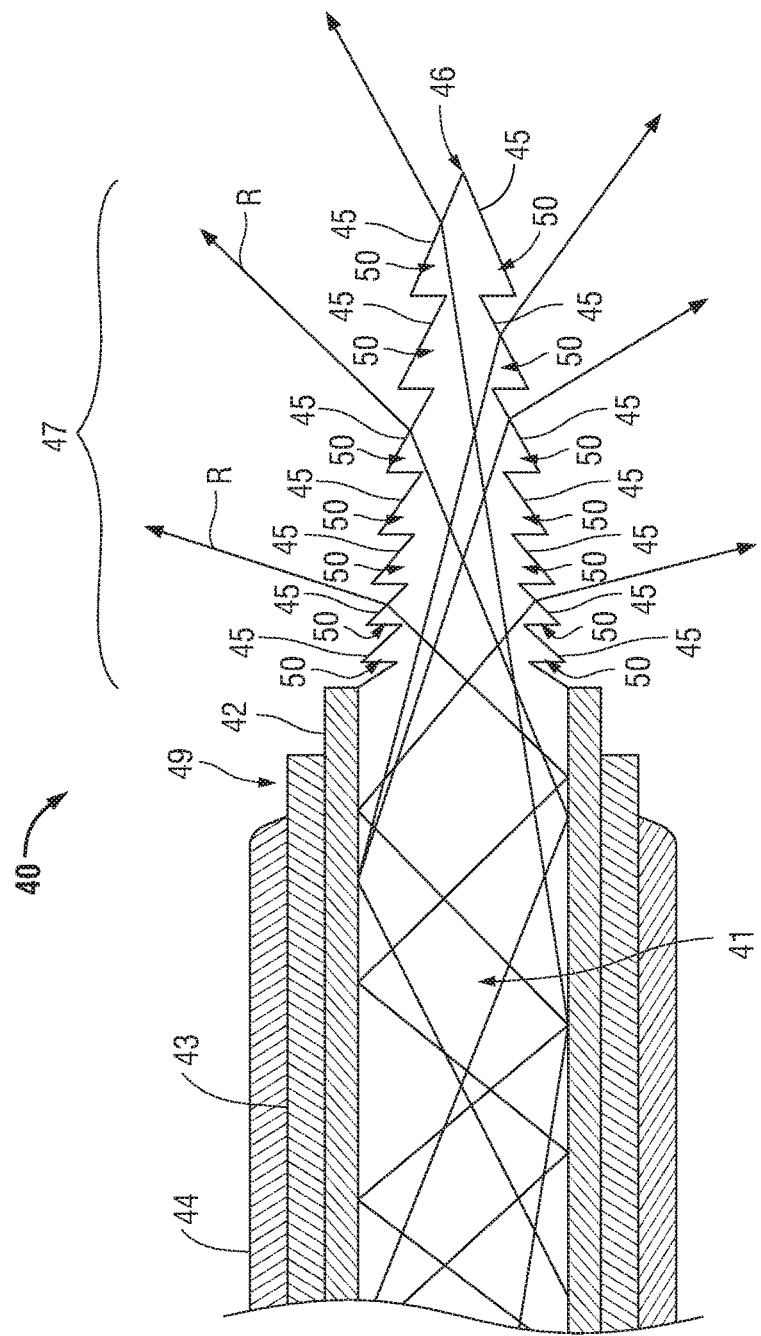
FIG. 4A is a cross-sectional view of a laser surgery instrument, which includes tapered fiber optic terminus, to generate a tapered radiation pattern in accordance with an embodiment the present disclosure.
Figure 4B:
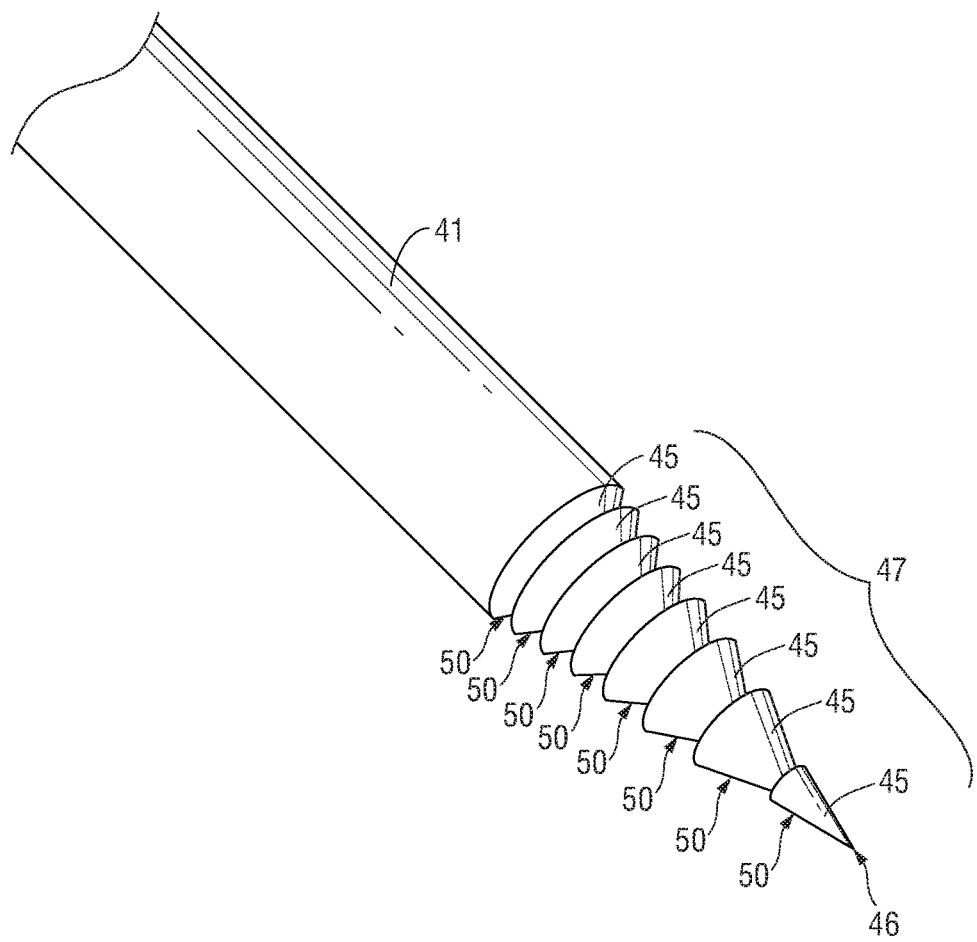
FIG. 4B is a perspective view of the tapered fiber optic terminus of the laser surgery instrument of FIG. 4A in accordance with the present disclosure.
Figure 4C:
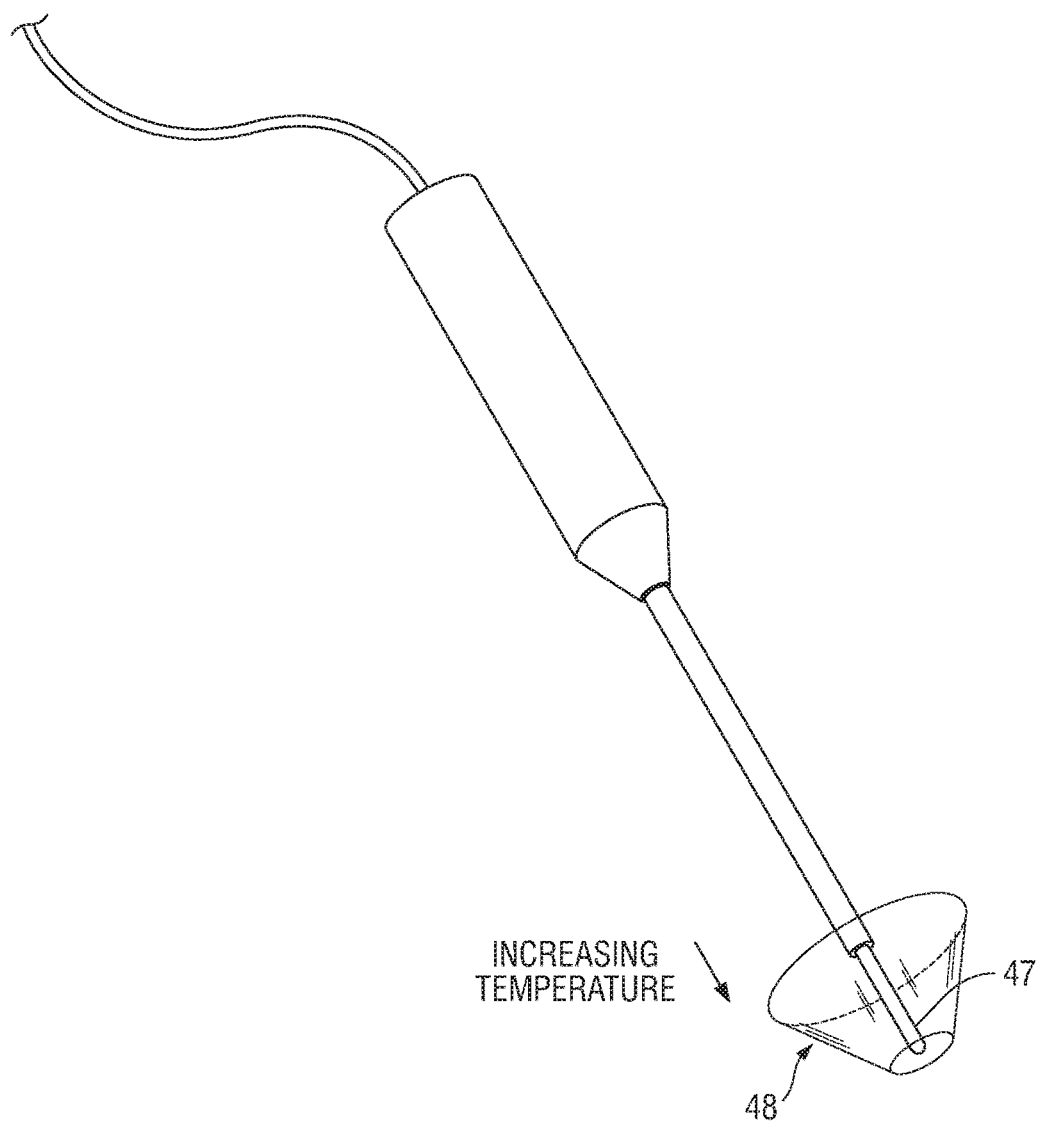
FIG. 4C is a perspective schematic view including a representation of a tapered pattern of thermal radiation of the laser surgery instrument of FIG. 4A.

Referring now to FIGS. 4A, 4B, and 4C, an embodiment of a tapered terminus 40 in accordance with the present disclosure is shown. Tapered terminus 40 includes a fiber optic assembly 49 that includes a core 41 coaxially disposed within a cladding 42, which, in turn, is coaxially disposed within a jacket 43. Fiber optic assembly 49 is longitudinally disposed within a shaft 44 of a laser surgery instrument (not explicitly shown) to facilitate the treatment of tissue therewith.

A portion of the fiber core 41 extends distally beyond the other elements of fiber optic assembly 49 and shaft 44 (e.g., extends distally beyond the distal end of the cladding 42, the jacket 49, and the shaft 44) to form a tapered tip 47 which includes a series of annular prisms 50 defined around the tapered tip 47, with each prism 50 having a refracting surface 45. In this embodiment and as best illustrated in FIGS. 4A and 4B, as the distance of each prism 50 from a distal end 46 of the radial tip 47 decreases, the prism angle of the corresponding refracting surface 45 of each prism also decreases. In addition, as the distance of each prism 50 from the distal end 46 decreases, the diameter of each prism also decreases, thus creating the tapered profile of the tapered tip 47. By this arrangement, during use, the rays R of laser energy which propagate distally through the fiber core 45 intersect the various one or more refracting surfaces 45 at an angle greater than the critical angle (not meeting the conditions for total internal reflection), which is based on the refractive indices of the fiber core 41 and the air, and thus exit the fiber core 41 in a tapered pattern 48 (FIG. 4C).

Figure 5C:
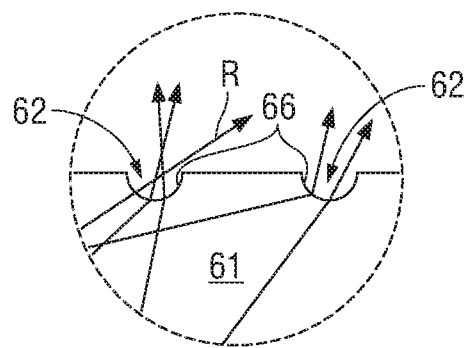
FIG. 5C is an enlarged, cross-sectional view of a portion of the fiber optic radial tip of FIG. 5A.

Referring now to FIGS. 5A, 5B, and 5C, still another embodiment of a fiber optic tip 60 is illustrated having a plurality of concave lenses 62 each having a refracting surface 66. The plurality of concave lenses 62 are defined in an outer surface 64 of a fiber core 61. As shown in FIGS. 5A and 5B, the plurality of concave lenses 62 are arranged in a regular pattern. However, the plurality of concave lenses 62 may be arranged in a random, pseudorandom, or arbitrary pattern. In addition, each of the plurality of concave lenses 62 may vary in size and shape from one another. For example, and without limitation, each of the plurality of concave lenses 62 may differ in diameter, depth, degree of concavity, and shape (e.g., ellipsoidal). As the laser rays R intersect the refracting surface 66 of each of the plurality of concave lenses 62 at an angle greater than the critical angle, no total internal reflection occurs, and consequently, the laser rays R exit the fiber core 61 in a generally radial pattern 68.

One or more concave lenses 62 may be defined in a distal end 63 of the fiber core 61. Additionally or alternatively, an opaque or semitransparent coating 65 may be disposed on the distal end 63 to reduce or eliminate laser emissions from the distal end 63. The use of one or more concave lenses 62 and/or an opaque or semitransparent coating 65 may help control the laser radiation pattern that emits from distal end 63 during the use.

Figure 5D:
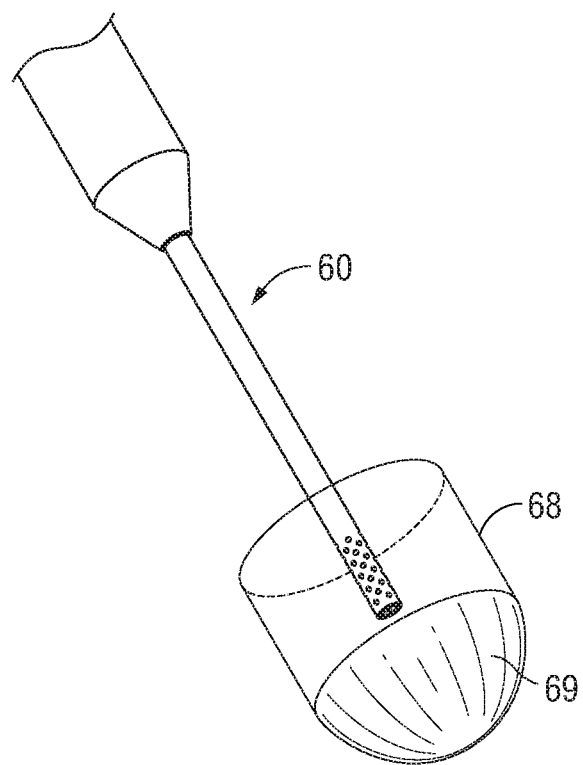
FIG. 5D is a schematic view including a representation of the radiation pattern of the fiber optic radial tip of FIG. 5A.

FIG. 5D illustrates a radiation pattern generated during the use of the fiber optic tip 60 of FIG. 5A where one or more concave lenses 62 are defined in the distal end 63 of the fiber core 61. As can be seen, this arrangement exhibits a generally radial pattern 68 with a hemispherical distal region 69 having an overall evenly-distributed temperature pattern.

Yet another embodiment of a fiber optic tip 70 is illustrated in FIGS. 6A and 6B wherein a plurality of concave lenses 72, each having a refracting surface 76, are defined in an outer surface 74 of a conically-tapered tip 75 of a fiber core 71. As shown, the plurality of concave lenses 72 are arranged in a random pattern. However, the plurality of concave lenses 72 may be arranged in a regular, pseudorandom, or arbitrary pattern. In addition, each of the plurality of concave lenses 72 may vary in size and shape from each another, e.g., a diameter, depth, degree of concavity, and shape (e.g., ellipsoidal) from one another. During a use of the fiber optic tip 70, the conically-tapered tip 75 and/or the arrangement of the plurality of concave lenses 72 function to generate a generally conical radiation pattern having an even temperature distribution.

The described embodiments of the present disclosure are intended to be illustrative rather than restrictive, and are not intended to represent every embodiment of the present disclosure. Further variations of the above-disclosed configurations of the described dissection instruments, and variations of these and other embodiments, and other features and functions, or alternatives thereof, may be made or desirably combined into many other different systems or applications without departing from the spirit or scope of the disclosure as set forth in the following claims both literally and in equivalents recognized in law.

What is claimed is:

1. An instrument for laser surgery, comprising:
    a cladding having a first refractive index;
    a fiber optic core coaxially disposed within the cladding and having a second refractive index that is higher than the first refractive index, the fiber optic core configured to operatively engage with a source of laser energy at a proximal end; and
    a fiber optic tip formed at a distal portion of the fiber optic core and configured to extend outwardly from the cladding, the fiber optic tip being exposed to air,
    wherein the fiber optic tip includes a plurality of refracting surfaces, each refracting surface formed at least at an angle relative to a longitudinal axis of the fiber optic tip and configured to disperse the laser energy in a radial pattern.

2. The instrument for laser surgery in accordance with claim 1, wherein the fiber optic tip includes a plurality of annular prisms.

3. The instrument for laser surgery in accordance with claim 2, wherein each one of the plurality of refracting surfaces is disposed on a corresponding one of the plurality of annular prisms.

4. The instrument for laser surgery in accordance with claim 2, wherein a diameter of each one of the plurality of annular prisms decreases as a distance of each one of the annular prisms from a distal end of the fiber optic tip decreases.

5. The instrument for laser surgery in accordance with claim 1, wherein an angle between each refracting surface and a longitudinal axis of the fiber optic core varies as a function of distance between each refracting surface and a distal end of the fiber optic tip.

6. The instrument for laser surgery in accordance with claim 5, wherein an angle of a first refracting surface is greater than an angle of a second refracting surface that is farther than the first refracting surface from the distal end of the fiber optic tip.

7. The instrument for laser surgery in accordance with claim 5, wherein an angle of each refracting surface decreases as a distance of each refracting surface from the distal end of the fiber optic tip decreases.

8. The instrument for laser surgery in accordance with claim 1, wherein each one of the plurality of refracting surfaces includes a concave lens defined in the fiber optic tip.

9. The instrument for laser surgery in accordance with claim 8, wherein a distal portion of the fiber optic tip on which the concave lenses are defined is tapered.

10. A laser surgery system comprising:
    a source of laser energy;
    a controller operatively coupled to the source of laser energy; and
    a laser surgical instrument, comprising:
        a cladding having a first refractive index;
        a fiber optic core coaxially disposed within the cladding and having a second refractive index that is higher than the first refractive index, the fiber optic core configured to be operatively engage with the source of laser energy at a proximal end; and
        a fiber optic tip formed on a distal end of the fiber optic core wherein the fiber optic tip extends outwardly from the cladding, the fiber optic tip being exposed to air,
        wherein the fiber optic tip includes a plurality of refracting surfaces, each refracting surface formed at least at one angle relative to a longitudinal axis of the fiber optic tip and configured to disperse the laser energy in a radial pattern.

11. The laser surgery system in accordance with claim 10, wherein the fiber optic core includes a plurality of annular prisms.

12. The laser surgery system in accordance with claim 11, wherein each one of the plurality of refracting surfaces is disposed on a corresponding one of the plurality of annular prisms.

13. The laser surgery system in accordance with claim 11, wherein a diameter of each one of the plurality of annular prisms decreases as the distance of each one of the annular prisms from a distal end of the fiber optic tip decreases.

14. The laser surgery system in accordance with claim 10, wherein an angle between each refracting surface and a longitudinal axis of the fiber optic core varies as a function of distance between each refracting surface and the distal end of the fiber optic tip.

15. The laser surgery system in accordance with claim 14, wherein an angle of a first refracting surface is greater than an angle of a second refracting surface that is farther than the first refracting surface from the distal end of the fiber optic tip.

16. The laser surgery system in accordance with claim 14, wherein an angle of each refracting surface decreases as a distance of each refracting surface from the distal end of the fiber optic tip decreases.

17. The laser surgery system in accordance with claim 10, wherein each one of the plurality of refracting surfaces includes a concave lens defined in the fiber optic tip.

18. The laser surgery system in accordance with claim 17, wherein a distal portion of the fiber optic tip on which the concave lenses are defined is tapered.

19. The laser surgery system in accordance with claim 10, further comprising a power supply operatively coupled to at least one of the controller or the source of laser energy.

* * * * *